United States Patent [19]

Felix

[11] Patent Number: 4,534,902
[45] Date of Patent: Aug. 13, 1985

[54] METHOD FOR PREPARATION OF N-PHOSPHONOMETHYLGLYCINE

[75] Inventor: Raymond A. Felix, Richmond, Calif.

[73] Assignee: Stauffer Chemical Company, Westport, Conn.

[21] Appl. No.: 630,156

[22] Filed: Jul. 12, 1984

Related U.S. Application Data

[60] Division of Ser. No. 540,254, Oct. 11, 1983, Pat. No. 4,476,063, which is a continuation-in-part of Ser. No. 391,033, Jun. 22, 1982, abandoned.

[51] Int. Cl.$^3$ .......................................... C07C 121/417
[52] U.S. Cl. ................................................... 260/465.4
[58] Field of Search ...................................... 260/465.4

[56] References Cited

U.S. PATENT DOCUMENTS

| | | | |
|---|---|---|---|
| 3,102,068 | 8/1963 | Tolbert | 260/465.4 X |
| 3,160,632 | 12/1964 | Dock Fon Toy et al. | 544/337 |
| 3,758,644 | 9/1973 | Stolzer et al. | 260/465.4 X |
| 3,799,758 | 3/1974 | Franz | 260/944 X |
| 3,923,877 | 12/1975 | Barton | 260/940 X |
| 3,966,789 | 6/1976 | Oishi et al. | 260/465.4 |
| 4,021,224 | 5/1977 | Pallos et al. | 260/465.4 |
| 4,197,254 | 4/1980 | Gaertner | 71/86 X |
| 4,199,354 | 4/1980 | Hinshaw et al. | 430/226 |
| 4,288,384 | 9/1981 | Walker | 260/465.4 X |
| 4,427,599 | 1/1984 | Felix | 260/465.4 X |

*Primary Examiner*—Joseph Paul Brust
*Attorney, Agent, or Firm*—Edwin H. Baker

[57] ABSTRACT

A method of preparing N-phosphonomethylglycine comprising (a) reacting a triazine with an acyl halide to form the N-cyanomethyl-N-halomethyl amide of the acyl halide; reacting the said amide with a phosphite to form a phosphonate compound; and hydrolyzing said phosphonate to yield N-phosphonomethylglycine.

3 Claims, No Drawings

METHOD FOR PREPARATION OF N-PHOSPHONOMETHYLGLYCINE

CROSS REFERENCE TO RELATED APPLICATIONS

This is a divisional, of application Ser. No. 540,254, filed Oct. 11, 1983, now, U.S. Pat. No. 4,476,063 which is a continuation-in-part of application Ser. No. 391,033, filed June 22, 1982 now abandoned.

FIELD OF THE INVENTION

This invention is a new process for preparing N-phosphonomethylglycine.

BACKGROUND OF THE INVENTION

N-Phosphonomethylglycine and certain salts are particularly effective as post-emergence herbicides. The commerical herbicide is sold as a formulation containing the isopropylamine salt of N-phosphonomethylglycine.

N-Phosphonomethylglycine can be made by a number of methods. One such method, as described in U.S. Pat. No. 3,160,632 is to react N-phosphinomethylglycine (glycinemethylenephosphonic acid) with mercuric chloride in water at reflux temperature, and subsequently separating the reaction products. Other methods are phosphonomethylation of glycine and the reaction of ethyl glycinate with formaldehyde and diethylphosphite. The latter method is described in U.S. Pat. No. 3,799,758. In addition, there is a series of patents relating to the preparation of N-phosphonomethylglycine, including U.S. Pat. Nos, 3,868,407, 4,197,254 and 4,199,354.

Close prior art is U.S. Pat. No. 3,923,877, which teaches the reaction of 1,3,5-tricyanomethylhexahydro-1,3,5-triazine with excess di-substituted phosphite to form $(RO)_2P(O)CH_2NHCH_2CN$ (R is hydrocarbyl or substituted hydrocarbyl) which is hydrolyzed to yield N-phosphonomethylglycine.

Because of the commercial importance of N-phosphonomethylglycine and certain salts as herbicides, improved methods of preparing these compounds are valuable.

BRIEF DESCRIPTION OF THE INVENTION

This invention relates to a process for preparing N-phosphonomethylglycine which comprises:

(1) reacting 1,3,5-tricyanomethylhexahydro-1,3,5-triazine with an acyl halide, preferably acyl chloride to form the N-cyanomethyl-N-halomethyl amide of the acyl halide;

(2) reacting the amide with a phosphite to form N-acylaminomethyl-N-cyanomethyl phosphonate; and (3) hydrolyzing this phosphonate to yield N-(phosphonomethyl)-glycine.

DETAILED DESCRIPTION OF THE INVENTION

The process of this invention may be illustrated by the following reaction scheme:

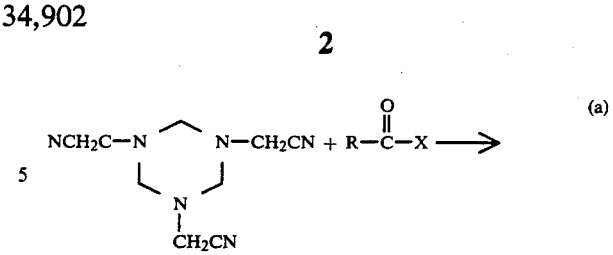

wherein R is an aliphatic or aromatic group as defined hereinafter, preferably $C_1$-$C_4$ alkyl, most preferably methyl or ethyl and X is chlorine, bromine, or iodine, preferably chlorine.

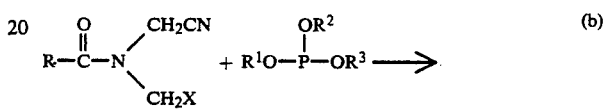

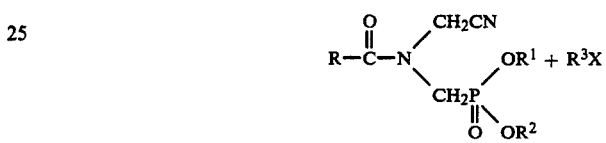

wherein R and X are defined as above and $R^1$ and $R^2$ are both aromatic groups or both aliphatic group, preferably $R^1$ and $R^2$ are $C_1$-$C_6$ alkyl, more preferably $C_1$-$C_4$ alkyl, and $R^3$ is an aliphatic group, preferably $R_3$ is $C_1$-$C_6$ alkyl, more preferably $C_1$-$C_4$ alkyl or $R^3$ is an alkali metal (M), preferably sodium or potassium.

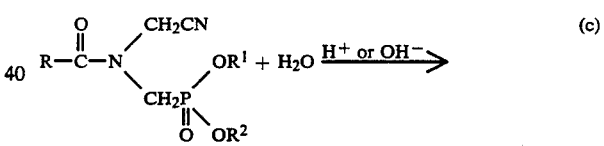

wherein R, $R^1$ and $R^2$ are as defined above and $H^+$ is a strong acid such as hydrochloric, hydrobromic, hydriodic, nitric, sulfuric, phosphonic or chloroacetic acid. Preferably $H^+$ is hydrochloric or hydrobromic acid and $OH^{31}$ is a strong base such as sodium hydroxide or potassium hydroxide, preferably in an aqueous, aqueous-alcoholic or alcoholic solution. Preferably, the hydroylsis is run in the presence of a strong acid.

In the above reaction scheme the group R is not directly involved in reaction step (a) between 1,3,5-tricyanomethylhexahydro-1,3,5-triazine and the acyl chloride. Groups R, $R^1$ or $R^2$ are not directly involved in reaction step (b) between the N-cyanomethyl-N-chloromethyl amide reaction product of step (a) and the phosphite. Groups R, $R^1$ and $R^2$ are removed in reaction step (c) when the phosphonate reaction product of reaction step (b) is subjected to hydrolysis. Therefore, the nature of groups R, $R^1$ and $R^2$ is not critical, although groups which would interfere with reaction steps (a) and (b) are to be avoided.

The group "$C_1$–$C_4$ alkyl" encompasses methyl, ethyl, n-propyl, isopropyl, n-butyl, isobutyl, sec-butyl, and tert-butyl. The group "$C_1$–$C_6$ alkyl" encompasses the same radicals as $C_1$–$C_4$ alkyl plus the 6 pentyls and the 16 hexyls.

The term "aliphatic group" is used in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

Reaction step (a) preferably is run at a temperature between about 0° to about 150° C., more preferably between about 40° to about 110° C. and most preferably between about 75° to about 85° C. This reaction step can be run at atmospheric, sub-atmospheric or super-atmospheric pressure, preferably at atmospheric pressure. Preferably the reaction is run in a solvent for the acyl halide, such as ethylene dichloride, methylene chloride, tetrahydrofuran or toluene.

Three moles of the acyl halide are needed to react with one mole of the 1,3,5-tricyanomethylhexahydro-1,3,5-triazine. An excess of acyl halide can be used to insure complete reaction with the triazine. A large excess of the acyl halide can serve as a solvent in this reaction step. The solvent or any excess acyl halide can be removed to isolate the N-cyanomethyl-N-chloromethyl amide of the acyl halide in high yields. However, this amide quickly degrades thermally and by hydrolysis and should be kept in an inert atmosphere if isolated.

Most preferably no excess acyl halide is used and the solvent used in reaction step (a) is also used as the solvent in reaction step (b). Thus, no solvent need be removed after completion of step (a) and it is used in reaction step (b).

In reaction step (b), most preferably about equal mole amounts of N-cyanomethyl-N-halomethyl amide of the acyl halide and the phosphite are reacted. Less preferably, up to 2 mole excess can be used and least preferably up to a 10 mole excess can be used.

The reaction is exothermic and can be run at a temperature between about 0° to about 150° C., more preferably between about 40° to about 100° C.; most preferably between 75° to about 85° C.

No solvent is needed for the reaction, however, any inert solvent can be used, preferably the solvent having a boiling point between about 40° to about 100° C. Examples of such solvents are ethylene chloride, methylene chloride, tetrahydrofuran and toluene. The use of an inert solvent helps dissipate the heat of reaction. Most preferably the solvent is the one used in reaction step (a). Any solvent used in this reaction step will be removed after completion of reaction step (c), so preferably it is one that can be removed by evaporation.

Alkali metal phosphites having the formula

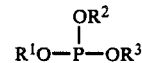

wherein $R^1$ and $R^2$ are as defined and $R^3$ is an alkali metal are reacted with N-cyanomethyl-N-halomethyl amide under an inert atmosphere such as nitrogen. The alkali metal phosphite can be prepared by reacting an alkali metal alkoxide, alkali metal hydride or alkali metal with an equal mole amount of a disubstituted phosphite of the formula

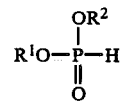

wherein $R^1$ and $R^2$ are as defined. This reaction is run in an inert atmosphere such as nitrogen.

Alkali metal phosphites of the formula

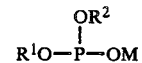

where $R^1$, $R^2$ and M are as defined can, because of tautomerism, have the following additional structural formula

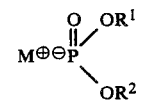

wherein $R^1$ and $R^2$ are as defined and M is an alkali metal.

In reaction step (c), a mole of the phosphonate reaction product from reaction step (b) is hydrolyzed with 5 moles of water. The hydrolysis is run in the presence of a strong acid or base as defined above. Preferably the hydrolysis is acid-catalyzed, preferably with an inorganic acid, and most preferably with hydrochloric or hydrobromic acid. The hydrolysis yields the desired N-phosphonomethylglycine. Preferably at least 2 moles of the acid are used. more preferably, a large excess over the 2 mole amount is used. The preferred hydrochloric or hydrobromic acid can be used in concentrated or aqueous form.

This last reaction step is run at a temperature between about 0° to about 200° C., preferably between about 50° to about 125° C. and most preferably between about 100° to about 125° C.

Atmospheric, sub-atmospheric or super-atmospheric pressure can be used. Preferably atmospheric pressure is used during the hydrolysis.

The solid N-phosphonomethylglycine can be recovered by conventional techniques in reaction step (c). Volatile liquid products such as alcohols (methanol) chlorides (methyl chloride), acids (acetic acid), water, and excess acid can be removed by standard stripping techniques. The desired N-phosphonomethylglycine is recovered in high purity by dissolving it in water, adjusting the pH of the solution to between 1 and 2, allowing it to crystallize from solution and removing it by filtration.

The process of this invention can be better understood by reference to the following specific examples.

EXAMPLE 1

Preparation of N-cyanomethyl-N-chloromethylacetamide $$CH_3-\overset{\overset{O}{\|}}{C}-N\overset{CH_2CN}{\underset{CH_2Cl}{\diagdown}}$$

Seventeen grams (g) (0.0835 mole) of 1,3,5-tricyanomethylhexahydro-1,3,5-triazine were slurried in a round-bottom flask with 150 milliliters (ml) of 1,2-dichloroethane. Forty ml (0.563 mole) acetyl chloride were added all at once and the reaction mixture was refluxed 3 hours, then stripped under reduced pressure to yield 26.9 g (79.85%) N-cyanomethyl-N-chloromethylacetamide. Structure was confirmed by usual analytical methods (infrared, proton nuclear magnetic resonance, and mass spectroscopy).

EXAMPLE 2

Preparation of 0,0-dimethyl-N-cyanomethyl-N-acetylaminomethyl phosphonate $$CH_3-\overset{\overset{O}{\|}}{C}-N\overset{CH_2CN}{\underset{CH_2\underset{\overset{\|}{O}}{P}-(OCH_3)_2}{\diagdown}}$$

The amide compound prepared in Example 1 (26.9 g, 0.2 mole) was diluted with 75 ml of dichloromethane. Trimethyl phosphite (25.5 g, 0.206 mole) was added and the mixture was stirred at room temperature overnight, refluxed 0.5 hour and stripped under reduced pressure to yield 34.9 g (79.32%) of the desired product. The structure was confirmed by infrared (ir), proton nuclear magnetic resonance (nmr) and mass spectroscopy (ms).

EXAMPLE 3

Preparation of N-phosphonomethylglycine $$H-N\overset{CH_2-\overset{\overset{O}{\|}}{C}-OH}{\underset{CH_2\underset{\overset{\|}{O}}{P}-(OH)_2}{\diagdown}}$$

The phosphonate reaction product of Example 2 (19.5 g, 0.09 mole) was combined with 100 ml (1.21 mole) of concentrated hydrochloric acid, refluxed 3 hours, and stripped under reduced pressure. After dissolving the residue in 30 ml water, the pH was adjusted to 10 with 50% sodium hydroxide, the mixture was stripped under reduced pressure. The product was again dissolved in 30 ml water and the pH was adjusted to 1 with concentrated hydrochloric acid. The mixture was refrigerated overnight and the next morning 5.4 g (98.3% purity by weight) of the desired product were isolated by filtration (35.49% yield). Structure was confirmed by ir, nmr, and liquid chromatograph (lc).

EXAMPLE 4

Preparation of N-phosphonomethylglycine

Fifty milliliters of 1,2-dichlorethane were heated to reflux in a 50 ml round-bottom flask. Acetyl chloride (5.5 ml, 0.077 mole) and 3.4 g (0.0167 mole) of 1,3,5-tricyanomethylhexahydro-1,3,5-triazine were added simultaneously over 10 minutes while maintaining an excess of the acetyl halide in the reaction vessel. The mixture was refluxed for 0.5 hours after addition was complete then stripped under reduced pressure.

Five milliliters of toluene and 6.6 ml (0.05 mole) of trimethyl phosphite were added to the residue and this mixture was refluxed 15 minutes, stirred at room temperature for 2 hours and stripped under reduced pressure.

Thirty milliliters (0.36 mole) of concentrated hydrochloric acid were added to the residue and the mixture refluxed for 3 hours and stripped under reduced pressure to yield 11.3 g solids containing 47.9% by weight of the desired N-phosphonomethylglycine as determined by lc. Structure was confirmed by $C^{13}$ and proton nmr. Overall yield of N-phosphonomethylglycine was 64%.

EXAMPLE 5

Preparation of 0,0-dimethyl-N-cyanoethyl-N-carboethoxyaminomethyl phosphonate $$C_2H_5O-\overset{\overset{O}{\|}}{C}-N\overset{CH_2CN}{\underset{CH_2\underset{\overset{\|}{O}}{P}-(OCH_3)_2}{\diagdown}}$$

Ethylchloroformate (8 ml. 0.083 mole) dissolved in 8 ml methylene chloride and 3.4 g 1,3,5-tricyanomethylhexahydro-1,3,5-triazine (0.0167 mole) were combined in a 50 ml round-bottom flask equipped with a stirrer and reflux condenser. The mixture was refluxed for 1 hour and stripped under reduced pressure. The residue was dissolved in 5 ml methylene chloride. Trimethylphosphite (5 ml, 0.042 mole) dissolved in 15 ml methylene chloride was added. This reaction mixture was refluxed for 1 hour. To the cooled mixture 50 ml of water was added. The mixture was extracted three times with 50 ml of methylene chloride. The organic portions were combined and dried with magnesium sulfate and stripped under vacuum to yield 6.9 g of the desired product which is a 50 percent yield. The structure was confirmed by ir, nmr and ms.

EXAMPLE 6

Preparation of N-phosphonomethylglycine

The phosphonate reaction product of Example 5 (4.9 g, 0.02 mole) was combined with 20 ml (0.24 mole) of concentrated hydrochloric acid, refluxed 3 hours, and stripped under reduced pressure. After dissolving the residue in 30 ml water, the pH was adjusted to 10 with 50% sodium hydroxide, and the mixture was stripped under reduced pressure. The product was again dissolved in about 5 ml water. Structure was confirmed by nmr, and liquid chromatograph (lc).

EXAMPLE 7

Preparation of
0,0-diethyl-N-cyanomethyl-N-acetylaminomethyl phosphonate

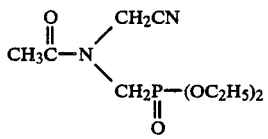

Five and six-tenths grams (5.6 g, 0.05 m) of potassium-t-butoxide were slurried in a round bottom flask with 25 ml of tetrahydrofuran (dried over molecular sieves) and the slurry was cooled in a water bath. Next 6.44 ml (0.05 m) of diethyl phosphite were added dropwise to the slurry over 5 minutes, under nitrogen. This mixture was cooled in an ice bath and 7.33 g (0.05 m) of N-cyanomethyl-N-chloromethylacetamide diluted with 50 ml of tetrahydrofuran were added dropwise over 15 minutes. The mixture was allowed to warm to room temperature and stirred for 3 hours. The mixture was filtered through dicalite and the tetrahydrofuran stripped under reduced pressure to yield 9.0 g of the desired product. Structure was confirmed by ir, nmr, ms, C-13 nmr.

EXAMPLE 8

Preparation of Phosphonomethylglycine

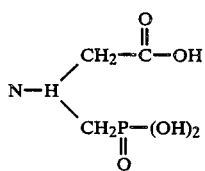

Five and four-tenths grams (5.4 g, 0.022 m) of the compound prepared in Example 7 were combined with 30 ml (0.363 m) of concentrated HCl, refluxed 3 hours and then stripped under reduced pressure to yield 10.8 g of the desired product, a brown semi-solid. Structure was confirmed by ir, nmr, C-13 nmr, and lc techniques.

EXAMPLE 9

Preparation of
0,0-dimethyl-N-cyanomethyl-N-acetylaminomethyl phosphonate

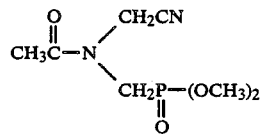

One and forty-four-one hundredths grams (1.44 g, 0.06 m) of sodium hydride were slurried with 25 ml of tetrahydrofuran (dried over molecular sieves) under dry nitrogen. Six and forty-tenths ml (0.05 m) of dimethylphosphite were added dropwise over 15 minutes. When all hydrogen gas had evolved the mixture was cooled in an ice bath and 7.33 g (0.05 m) of N-cyanomethyl-N-chloromethylacetamide, diluted with 50 ml dry tetrahydrofuran, were added dropwise over 15 minutes. The mixture was stirred overnight, filtered and stripped at reduced pressure to yield 11.5 g of the desired product, a yellow oil.

Structure was confirmed by ir, nmr, ms, C-13 nmr and glpc techniques.

The compound of Example 9 can be hydrolyzed to phosphonomethylglycine according to the teaching of Example 3.

I claim:
1. A compound of the formula

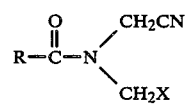

wherein R is $C_1$–$C_4$ alkyl or ethoxy and X is chlorine, bromine or iodine.

2. The compound of claim 1 wherein R is methyl and X is chlorine.

3. The compound of claim 1 wherein R is ethoxy and X is chlorine.

* * * * *